| United States Patent [19] | [11] 3,976,697 |
|---|---|
| Kuntschik et al. | [45] Aug. 24, 1976 |

[54] PREPARATION OF TERTIARY AMINES

[75] Inventors: Lawrence F. Kuntschik, Nederland; Orville W. Rigdon, Groves, both of Tex.

[73] Assignee: Texaco Inc., New York, N.Y.

[22] Filed: Oct. 29, 1974

[21] Appl. No.: 518,336

[52] U.S. Cl. .................. 260/583 R; 260/563 C; 260/563 D; 260/585 C
[51] Int. Cl.² .................. C07C 87/00; C07C 87/02
[58] Field of Search ........ 260/583 R, 563 D, 563 C, 260/585 C

[56] References Cited
UNITED STATES PATENTS

| | | | |
|---|---|---|---|
| 2,160,058 | 5/1939 | Covert | 260/585 C |
| 3,091,641 | 5/1963 | Sweeney | 260/585 C |
| 3,235,515 | 2/1966 | Taylor | 260/563 D X |
| 3,442,951 | 5/1969 | Thirion | 260/583 R |
| 3,520,933 | 7/1970 | Adam et al. | 260/583 R X |
| 3,597,438 | 8/1971 | Brake | 260/583 R X |
| 3,873,621 | 3/1975 | Kreevoy | 260/585 C |

FOREIGN PATENTS OR APPLICATIONS

| | | |
|---|---|---|
| 1,182,562 | 2/1970 | United Kingdom |

OTHER PUBLICATIONS

Wagner et al., Synthetic Organic Chemistry, John Wiley & Sons, Inc., N.Y., pp. 662 & 663 (1953).

*Primary Examiner*—Helen M. S. Sneed
*Attorney, Agent, or Firm*—T. H. Whaley; C. G. Ries; George J. Darsa

[57] ABSTRACT

Reductive amination of $C_{10}$–$C_{26}$ dialkyl internal ketones, with secondary amines, using a supported nickel catalyst, results in the production of tertiary amines in excellent yield.

18 Claims, No Drawings

PREPARATION OF TERTIARY AMINES

BACKGROUND OF THE INVENTION

This invention relates to the production of long chain tertiary amines by reductive amination of $C_{10}$–$C_{26}$ alkyl ketones with secondary amines. More particularly, it relates to a process for the reductive amination of $C_{10}$–$C_{26}$ dialkyl internal ketones to obtain tertiary amines in high yield. Still more particularly, it relates to the reductive amination of said ketones with secondary amines using a supported nickel catalyst.

The preparation of tertiary amines by the general process of reductive alkylation of ketones and aldehydes with amines is well known and has been thoroughly reviewed in *Organic Reactions*, Volume 4, chapter 3 (1948). Reductive amination is accomplished by reacting the aldehyde or ketone with the amine and hydrogen in the presence of a supported metal catalyst, the metal being, for example, nickel or a noble metal such as platinum or palladium. Primary emphasis is on the reaction of low molecular weight aldehydes and ketones with ammonia and low molecular weight amines, using mainly platinum as the catalyst. The preparation of tertiary amines by the reaction of ketones and secondary amines is disclosed, using a platinum catalyst, with yields up to about 47% of the theoretical amount.

From the discussion and data presented in *Organic Reactions*, Volume 4, it appears that reductive amination with secondary amines, using platinum or palladium catalysts, gives rather low yield of product tertiary amine. On page 207 of said reference, a tabulation is set out showing alkylation of various ketones with methyl-sec.butyl amine. With acetone the yield of tertiary amine product is 47%. A sharp decline in yield is observed as the molecular weight of the methyl ketone reactant is increased such that for methylethyl ketone the yield is 18%, for methyl-n-butyl ketone the yield is 8% and for 2-octanone the yield is merely 0.6%. Thus, for methyl ketones, it would appear that the reductive amination reaction to obtain tertiary amines provides satisfactory yields only for the extremely low molecular weight ketones.

If one wishes to obtain tertiary amines from internal ketones, i.e., high alkyl ketones in which each alkyl group has 2 or more carbon atoms, the process taught in *Organic Reactions*, Volume 4, would appear to be virtually useless. The reaction of methyl-sec.butyl amine with diethyl ketone, the lowest molecular weight internal ketone, using a platinum catalyst results in tertiary amine of only 0.02% yield.

Accordingly, it is an object of this invention to develop a process for the preparation of tertiary amines by the reductive amination of internal ketones having from 10 to 26 carbon atoms, particularly those having from 10 to 13 carbon atoms. It is a further object to develop such a reductive amination process with sufficiently high product yield so as to be commercially feasible.

SUMMARY OF THE INVENTION

Tertiary amines having at least 1 alkyl group of 10 to 26 carbon atoms, are prepared by reductive amination of internal ketones having from 10 to 26 carbon atoms, using a supported nickel catalyst. The product is obtained in excellent yield.

DETAILED DISCLOSURE

The dialkyl ketone reactants have the structural formula:

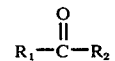

in which each of $R_1$ and $R_2$ is independently alkyl of from 2 to 24 carbon atoms and the sum of the carbon atoms in $R_1$ and $R_2$ is from 10 to 26. These ketone reactants are termed "internal ketones", since neither $R_1$ nor $R_2$ is methyl. Examples of such ketone starting materials include 3-decanone, 4-decanone, 5-decanone, 3-undecanone, 4-undecanone, 5-undecanone, 6-undecanone, 3-dodecanone, 4-dodecanone, 5-dodecanone, 6-dodecanone, 3-tridecanone, 4-tridecanone, 5-tridecanone, 6-tridecanone, 7-tridecanone, 7-tetradecanone, 8-pentadecanone, 7-hexadecanone, 9-heptadecanone, 5-octadecanone, 10-nonadecanone, 8-eicosanone, didecyl ketone, decyl-undecyl ketone and 12-tricosanone. The ketone reactant may consist of a single compound or it may be a mixture of isomers or a mixture of $C_{10}$–$C_{13}$, $C_{13}$–$C_{26}$ or $C_{10}$–$C_{26}$ ketones having the appropriate total carbon content. The ketones may be prepared by methods well known in the art, such as, for example, by hydrolysis of the corresponding oximes which, in turn, may be prepared by nitrosation of the corresponding n-paraffins.

The secondary amine reactant has the formula:

in which each of $R_3$ and $R_4$ is independently alkyl of from 1 to 10 carbon atoms or cycloalkyl of from 3 to 10 carbon atoms. Preferably, each of $R_3$ and $R_4$ is alkyl of from 1 to 4 carbon atoms, such as dimethylamine, methylethylamine, methyl-sec-butylamine and diethylamine. More preferably, the amine is dimethylamine.

The reductive amination reaction proceeds according to the following reaction scheme:

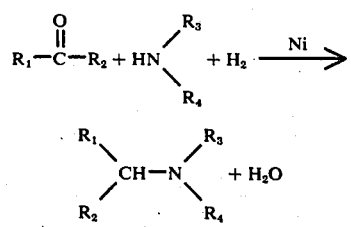

The catalyst employed herein, providing the improved conversion and selectivity in the amination reaction described above, is nickel supported or impregnated on or in a conventional catalyst base or support material such as kieselguhr, alumina, silica, silica-alumina, silica gel, carbon, pumice, porcelain, quartz, asbestos and the like, and we prefer to employ keiselguhr. Such catalysts may be prepared by various methods well known in the art, such as contacting the appropriate support material with an aqueous solution of inorganic nickel compounds to adsorb the nickel on the support followed by calcination at elevated temperatures. Sintered nickel catalysts may be prepared as described in U.S. Pat. No. 3,253,248. A highly preferred catalyst is zirconium modified nickel. Methods for preparing the preferred zirconium modified nickel catalysts are described in U.S. Pat. No. 3,235,515 which is hereby incorporated by reference. The amount of zirconium calculated as metal is in the range of 2 to 10% based on the weight of nickel and where support catalysts are contemplated, the zirconium modified nickel may constitute from about 0.1 to 60% or more of the catalyst composition.

The reductive amination reaction may be advantageously conducted by charging the ketone, secondary amines and catalyst to a hydrogenation reactor, pressuring the reactor with hydrogen and heating to reaction temperature. Reaction pressure may range from atmospheric to about 3000 psig, preferably from about 100 to about 2000 psig. Reaction temperatures may vary widely from about 0° to about 400°F.; convenient reaction temperatures are in the range of about 100° to about 300°F. The choice of pressure and temperature conditions will depend on various factors, such as equipment available, physical constants of the reactant products, cost, etc., and other factors well known to persons skilled in the art. The amine reactant can be added to the reactor dissolved in a solvent or simply pressured into the reactor as a gas. When a solvent is used, it may be, for example, a low molecular hydrocarbon, alcohol, or cyclic ethers, such as $C_1$–$C_6$ alkanes, $C_4$–$C_8$ cycloalkanes $C_1$–$C_6$ alcohols, tetrahydrofuran and dioxane. Again, the choice of solvent to be used will depend upon various factors known to persons skilled in the art, including temperature and pressure. Preferred solvents are the low molecular weight alcohols such as methanol, ethanol and isopropanol or cyclic ethers such as tetrahydrofuran and dioxane. When the amine reactant is charged as a gas, there will be a corresponding increase in reaction pressure.

Reaction times can vary from 0.5 to 20 hours; conveniently, reaction times will be between about 2 to 10 hours. When the reaction is complete, the catalyst is removed, and the crude tertiary amine product can be separated from unreacted ketone and secondary amine by methods conventional in the art such as, for example, by vacuum fractionation. The product may then be purified by methods well known in the art.

The tertiary amine products produced according to the process of this invention are usable as fuel oil stabilizers and chemical intermediates. They can be economically converted to aliphatic amine oxides, which are currently in use as fabric softeners and conditioners. Additionally, they may be used as intermediates in the production of other chemicals.

The process of this invention, while specifically directed to reductive amination of internal ketones is also useful for reductive amination of mixed stream of $C_{10}$–$C_{26}$, $C_{10}$–$C_{13}$ or $C_{13}$–$C_{26}$ ketones containing methyl ketones and internal ketones. Typically these mixed streams contain from about 5 to about 95 wt. % internal ketones, more typically from about 50 to 90 wt. % internal ketones. The increased yield of tertiary amines obtained from the internal ketones will result in increased overall yield of mixed tertiary amines from the mixed ketone stream.

The process of this invention will be better understood by reference to the following specific examples, which are here included for purposes of illustration only and are not to be construed as limitations.

EXAMPLE 1

Reductive amination of 2-undecanone with a nickel catalyst.

46.2 grams of 2-undecanone, 46.0 grams of a commercially available zirconium modified nickel on kieselguhr catalyst composed of 50 wt. % nickel and 2 wt. % zirconium or kieselguhr, and 146.2 grams of a methanol solution saturated with dimethylamine were charged to a 1 liter Parr rocker-type reactor and quickly purged with nitrogen. After pressuring the reactor to 500 psig with hydrogen, the reactor and its contents were heated to 212°F. in a 2 hour period. Maximum reactor pressure was 640 psig.

The reaction was allowed to continue for 3.5 hours, at which time the reactor pressure remained constant. After cooling, the crude product was decanted from the catalyst and the catalyst was washed with anhydrous methanol. The decanted liquid and methanol washes were combined and centrifuged to remove catalyst fines. After removal of methanol by vacuum stripping, 53 grams of product containing 90.7 wt. % of N,N-dimethyl-2-undecylamine was obtained.

EXAMPLE 2

Reductive amination of 2-undecanone with a dimethylamine using a platinum catalyst.

46.2 grams of 2-undecanone, 46.0 grams of a commercially available catalyst comprising 0.375% platinum on alumina, and 146.2 grams of methanol saturated with dimethylamine were reacted according to the method of Example 1. The maximum pressure during heating was 620 psig. After 6 hours at 212°F., and approximately 550 to 620 psig, the reaction mixture was cooled and processed as in Example 1. The cooled product contained 96.7 wt. % of N,N-dimethyl-2-undecylamine and 0.3 wt. % of 2-undecanone.

EXAMPLE 3

Reductive amination of 6-undecanone with dimethylamine using a nickel catalyst.

46.2 grams of 6-undecanone, 46.0 grams of the nickel catalyst as in Example 1, and 150 grams of methanol saturated with dimethylamine were reacted according to the method of Example 1. Maximum reactor pressure was 660 psig. After removal of the methanol from the centrifugate by vacuum stripping, 52.7 grams of product containing 82.4 wt. % of N,N-dimethyl-6-undecylamine was obtained.

EXAMPLE 4

Reductive amination of 6-undecanone with dimethylamine using a platinum catalyst.

46.2 grams of 6-undecanone, 46.0 grams of catalyst as in Example 2, and 146.2 grams of methanol saturated with dimethylamine were reacted according to the method of Example 1. The maximum pressure during heating was 680 psig. After 6 hours at 212°F. and approximately 570 to 680 psig, the reaction mixture was cooled and processed as in Example 1. The crude product contained 67.7 wt. % of N,N-dimethyl-6-undecylamine and 26.9 wt. % of 6-undecanone.

The significantly higher yield of tertiary amine obtained from the internal ketone 6-undecanone when a nickel catalyst is employed (Example 3) than when a platinum catalyst is employed (Example 4) is quite surprising. When the ketone is a methyl ketone, such as 2-undecanone (Examples 1 and 2), reductive amination with either nickel or platinum gives tertiary amine products in good yield, with platinum showing somewhat better results.

The increased yield of tertiary amines from internal ketones resulting from the process of this invention makes possible the obtaining of a mixed stream of tertiary amines in good yield when the starting material is a mixture of $C_{10}$–$C_{26}$ ketones, $C_{10}$–$C_{13}$ ketones, or $C_{13}$ to $C_{26}$ ketones such as are produced in refining operations.

EXAMPLE 5

Reductive amination of mixed $C_{10}$–$C_{13}$ ketones with dimethylamine using a nickel catalyst.

46.0 grams of a mixture of various $C_{10}$–$C_{13}$ ketones including both methyl ketones (16.5%) and internal ketones (83.5%), 46.0 grams of a nickel catalyst as in Example 1 and 200 grams of a methanol solution saturated with dimethylamine were reacted according to the method of Example 1. The maximum reactor pressure was 685 psig. After 10 hours at 212°F. and 550 to 600 psig, the reaction mixture was cooled and processed as in Example 1. The product was 53.4 grams and contained 88.3 wt. % of N,N-dimethyl $C_{10}$–$C_{13}$ alkylamines.

EXAMPLE 6

Reductive amination of mixed $C_{10}$–$C_{13}$ ketones with dimethylamine using a platinum catalyst.

Example 5 was repeated except that the catalyst as in Example 2 was used (46.0 grams) instead of the nickel catalyst. The maximum reactor pressure was 690 psig. After 10 hours at 212°F. and 570–650 psig, the reaction mixture was cooled and processed as in Example 1. The crude product analyzed 35.6 wt. % N,N-dimethyl $C_{10}$–$C_{13}$ alkylamines and 63.2 wt. % unconverted to $C_{10}$–$C_{13}$ ketones.

A comparison of the results of Examples 5 and 6 shows the advantage of the process of this invention as applied to a $C_{10}$–$C_{13}$ ketone stream.

EXAMPLE 7

Reductive amination of 6-undecanone with methyl-sec.butylamine using a platinum catalyst.

46.2 grams of 6-undecanone, 46.0 grams of catalyst as in Example 2 and 200 grams of a solution of methanol and methyl sec-butylamine (containing 170.7 grams methanol and 29.3 grams amine) were reacted according to the method of Example 1. The maximum pressure during heating was 650 psig. After 6 hours at 212°F. the pressure remained constant at 620 psig indicating no further reaction. The reaction mixture was cooled and processed as in Example 1. The crude product contained 15.5 wt. % N-methyl-N-sec-butyl-6-undecylamine and 82.3 wt. % 6-undecanone.

EXAMPLE 8

Reductive amination of 6-undecanone with methyl-sec.butylamine using a nickel catalyst.

Example 7 was repeated except that the catalyst as in Example 1 (46.0 grams) was used instead of the platinum catalyst. The maximum pressure increase during heating was 620 psig. After 5 hours at 212°F. and approximately 550–600 psig, the reaction mixture was cooled and processed as in Example 1. The crude product contained 86.5 wt. % N-methyl-N-sec.butyl-6-undecylamine and 10.4 wt. % 6-undecanone.

EXAMPLE 9

Reductive amination of caprylone with dimethylamine using a nickel catalyst.

61.4 grams of caprylone (8-pentadecanone), 46.0 grams of catalyst as in Example 1 and 146.2 grams of dimethylamine-saturated methanol were reacted according to the method of Example 1. The maximum pressure during heating was 685 psig. After 6 hours at 212°F. and approximately 550–630 psig, the reaction mixture was cooled and processed as in Example 1. The crude product was analyzed by high speed liquid chromatography and found to contain 98.2 wt. % N,N-dimethyl-8-pentadecylamine and 1.5 wt. % unconverted caprylone.

EXAMPLE 10

Reductive amination of caprylone with dimethylamine using a platinum catalyst.

Example 9 was repeated except that the catalyst as in Example 2 was used (46.0 grams) instead of the nickel catalyst. Maximum pressure during heating was 700 psig. After 12 hours at 212°F. and approximately 650–690 psig, the reaction mixture was cooled and processed as in Example 1. Analysis of the crude product by high speed liquid chromatography showed the presence of 95.0 wt. % unconverted caprylone.

A comparison of Example 8 with Example 7 and of Example 9 with Example 10 again shows the significantly higher yield of tertiary amines from internal ketones where one employs a nickel catalyst rather than a platinum catalyst.

EXAMPLE 11

Reductive amination of 6-undecanone with dimethylamine using a nickel catalyst.

Example 3 was repeated using 150 grams of tetrahydrofuran saturated with dimethylamine instead of methanolic dimethylamine. Maximum reactor pressure was 670 psig. After removal of the tetrahydrofuran from the centrifugate by vacuum stripping, 51.3 grams of product containing 80.6 wt. % N,N-dimethyl-6-undecylamine was obtained.

EXAMPLE 12

Reductive amination of 6-undecanone with dimethylamine using a nickel catalyst.

Example 3 was repeated using 150 grams of dioxane saturated with dimethylamine instead of methanolic dimethylamine. The maximum reactor pressure was 640 psig. After removal of the dioxane from the centrifugate by vacuum stripping, 50.5 grams of product containing 81.2 wt. % N,N-dimethyl-6-undecylamine was obtained.

EXAMPLE 13

Reductive amination of mixed $C_{13}$–$C_{26}$ ketones with dimethylamine using a nickel catalyst.

80.0 grams of a mixture of various $C_{13}$–$C_{26}$ ketones including both methyl ketones (10.5 wt. %) and internal ketones (89.5 wt. %), 46.0 grams of the catalyst used in Example 1 and 200 grams of dioxane solution saturated with dimethylamine was reacted according to Example 1. The maximum pressure was 670 psig. After 12 hours at 212°F. and 550 to 625 psig, the reaction mixture was cooled and processed as in Example 1. The product (82.3 grams) contained 81.3 wt. % N,N-dimethyl $C_{13}$–$C_{26}$ alkylamines.

What is claimed is:

1. A process for the manufacture of tertiary amines of the formula

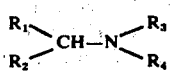

which each of $R_1$ and $R_2$ is alkyl of from 2 to 24 carbon atoms and the sum of the carbon atoms in $R_1$ and $R_2$ is from 10 to 26, and each of $R_3$ and $R_4$ is alkyl of from 1 to 10 carbon atoms or cycloalkyl of from 3 to 10 carbon atoms, which process consists essentially of reacting a ketone of the formula

with a secondary amine of the formula

and hydrogen in the presence of a supported nickel catalyst at a pressure of from about 100 to 2000 p.s.i.g. and a temperature of from about 100° to about 300°F.

2. A process according to claim 1 in which each of $R_1$ and $R_2$ is alkyl of from 2 to 11 carbon atoms and the sum of the carbon atoms in $R_1$ and $R_2$ is from 10 to 13.

3. A process according to claim 2 in which each of $R_3$ and $R_4$ is alkyl of from 1 to 4 carbon atoms.

4. A process according to claim 3 in which the secondary amine is dimethylamine.

5. A process according to claim 3 in which the secondary amine is methyl-sec.butylamine.

6. A process according to claim 2 in which the ketone is 6-undecanone.

7. A process according to claim 2 in which the ketone is a mixed stream comprising ketones in which each of $R_1$ and $R_2$ has from 2 to 11 carbon atoms.

8. A process according to claim 1 in which the sum of the carbon atoms in $R_1$ and $R_2$ is from 13 to 26.

9. A process according claim 8 in which each of $R_3$ and $R_4$ is alkyl of from 1 to 4 carbon atoms.

10. A process according to claim 9 in which the secondary amine is dimethylamine.

11. A process according to claim 8 in which the ketone is caprylone.

12. A process according to claim 8 in which the ketone is a mixed stream comprising ketones in which each of $R_1$ and $R_2$ has from 2 to 24 carbon atoms.

13. A process according to claim 1 in which each of $R_3$ and $R_4$ is alkyl of from 1 to 4 carbon atoms, and said secondary amine is dissolved in a solvent selected from the group consisting of $C_1$–$C_6$ alkanes, $C_4$–$C_8$ cycloalkanes, $C_1$–$C_6$ alcohols, tetrahydrofuran and dioxane.

14. A process according to claim 13 in which the solvent is a $C_1$–$C_6$ alcohol.

15. A process according to claim 14 in which the solvent is methanol.

16. A process according to claim 13 in which the solvent is tetrahydrofuran.

17. A process according to claim 13 in which the solvent is dioxane.

18. A process according to claim 1 in which the catalyst is a zirconium-modified nickel catalyst in which the zirconium-modified nickel constitutes from about 0.1 to about 60 wt. % of the catalyst and the zirconium is present in an amount ranging from about 2 to about 10 wt. % of the nickel.

* * * * *